United States Patent [19]

Grossi et al.

[11] Patent Number: 4,917,082

[45] Date of Patent: Apr. 17, 1990

[54] RESECTOSCOPE ELECTRODE

[75] Inventors: Benedetto Grossi; Raymond Ainger, III, both of Stamford, Conn.

[73] Assignee: Circon Corporation, Santa Barbara, Calif.

[21] Appl. No.: 202,153

[22] Filed: Jun. 2, 1988

[51] Int. Cl.[4] .............................................. A61B 17/36
[52] U.S. Cl. ......................................... 606/46; 606/49
[58] Field of Search ............ 128/303.1, 303.13–303.17

[56] References Cited

U.S. PATENT DOCUMENTS

| | | | |
|---|---|---|---|
| D. 251,608 | 4/1979 | Cawood, Jr. et al. | D24/18 |
| D 251,609 | 4/1979 | Cawood, Jr. et al. | D24/18 |
| 2,008,525 | 7/1935 | Wappler | 128/303.15 |
| 3,597,582 | 8/1971 | Goode | 128/303.14 |
| 3,746,814 | 7/1973 | Lackey et al. | 128/303.14 |
| 3,752,159 | 8/1973 | Wappler | 128/303.15 |
| 3,850,162 | 11/1974 | Iglesias | 128/6 |
| 3,901,242 | 8/1925 | Storz | 128/303.15 |
| 4,132,227 | 1/1979 | Ibe | 128/4 |
| 4,134,406 | 1/1979 | Iglesias | 128/303.15 |
| 4,149,538 | 4/1979 | Mrava et al. | 128/303.15 |
| 4,474,174 | 10/1984 | Petruzzi | 128/303.15 |
| 4,538,610 | 9/1985 | Kubota | 128/303.15 |
| 4,726,370 | 2/1988 | Karasawa et al. | 128/303.15 |

OTHER PUBLICATIONS

The New Continuous Flow Resectoscope From American ACMI, May 1984.
"ACMI Continuous Flow Resectoscope" Jan. 1987.
"Operating and Maintenance Manual Continuous Flow Resectoscope" American ACMI, Apr. 1983.
"ACMI Adult Resectoscope Operating & Maintenance Manual", American ACMI, Jun. 1984.

Primary Examiner—Max Hindenburg
Attorney, Agent, or Firm—Perman & Green

[57] ABSTRACT

An electrode for use with a urological endoscope and a method for making the same. The electrode comprises an electrode lead, an electrode end and an electrode stabilizer. The stabilizer can stabilize the electrode proximate a distal region of a telescope and is made of a resilient material for resiliently mounting the electrode to the telescope. The electrode lead and electrode end can be made from a single conductor.

16 Claims, 2 Drawing Sheets

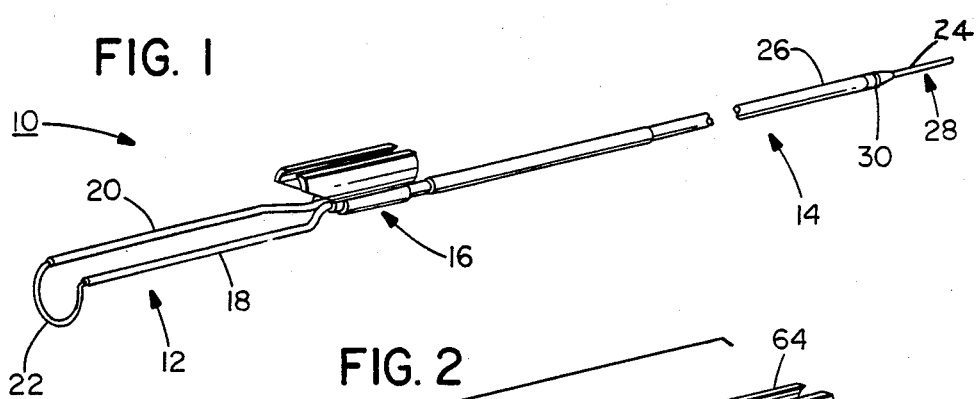
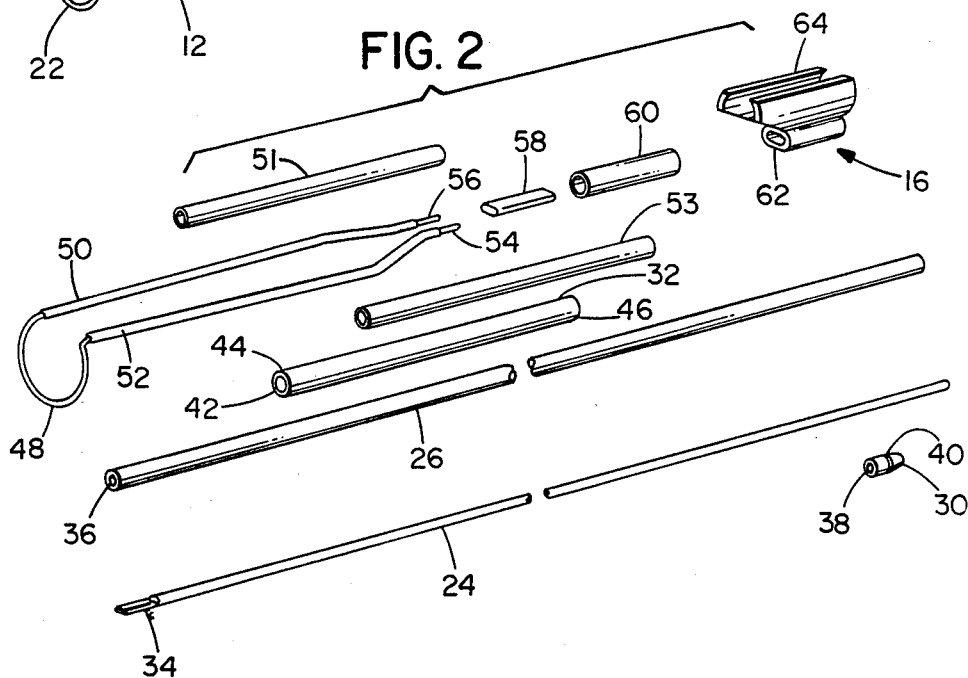
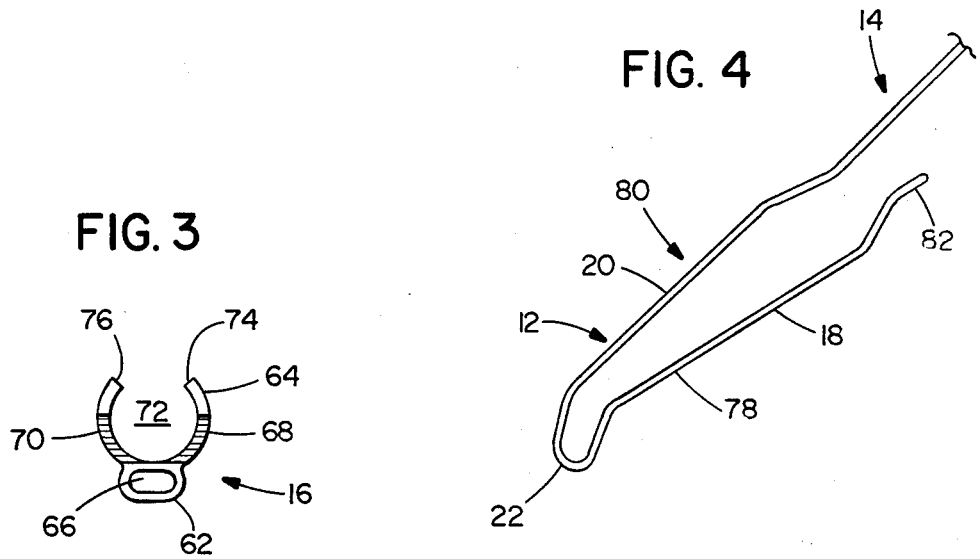
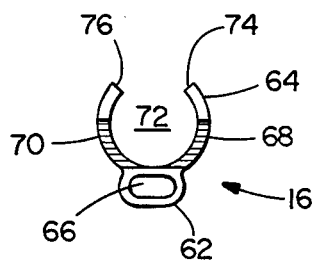

RESECTOSCOPE ELECTRODE

BACKGROUND OF THE INVENTION

1. Field of the Invention

This invention relates to medical endoscopes and, more particularly, to an improved electrode for use with a resectoscope and a method for making the same.

2. Prior Art

A typical resectoscope for transurethral resection consists of four main elements. The first element is a rigid telescope for observing the interior of the human bladder, or operative sites near the base of the urethra. The telescope comprises an objective lens and a series of relay lenses housed within an endoscope barrel or stem, the stem being connected to an eyepiece housing containing suitable lenses for proper magnification. The second element takes the form of a handle assembly commonly referred to as a working element. The working element can serve as the means for connecting electrosurgical current from an electrosurgical generator to the third element, an electrode assembly. The working element is also capable of slidably moving the electrode assembly axially, such axial movement being observable through the eyepiece of the telescope. The combination of the telescope, working element, and electrode assembly is locked into a fourth element, a resectoscope sheath. The sheath consists of a tube and a union body and lock assembly. In an operative procedure the sheath is placed into the urethra prior to introduction of the other elements.

The usual resectoscope electrode assembly takes the form of a U-shaped tungsten wire loop, the ends of the loop having integral spaced parallel wire arms which extend along, but are spaced from, the distal end of the rigid telescope. The wire arms usually merge at their proximal ends and are joined to an electrode lead extending back to the working element of the instrument. To brace the cutting loop so that it remains uniformly spaced from the telescope stem, a metal spacing sleeve is commonly provided between the telescope stem and either parallel electrode arms or the distal portion of the electrode lead immediately adjacent those arms. The metal spacing sleeve is slidable along the telescope stem as the electrode assembly is advanced and retracted and, because of the direct contact between the spacing sleeve and the telescope stem, it has been necessary in the past to insure adequate insulation between the electrode and the sleeve. Reference is made to U.S. Pat. Nos. 3,856,015, 3,901,242, 2,752,159, and 2,448,741 to illustrate prior cutting electrode assemblies.

U.S. Pat. No. 4,149,438 to Mrava et al discloses a plastic bearing tube for slidably engaging the rigid telescope stem of an instrument. Other electrodes in the prior art include members that have rigid seats that slidably sit on the rigid telescope stems and have a rigid stiffener over substantially the entire length of the electrode lead or merely a portion of the lead.

However, problems exist with electrodes of the prior art. Electrodes such as those disclosed in U.S. Pat. No. 4,149,538 must have the bearing tube slipped over the distal end of the telescope and do not have any type of stiffener for the distal region of the lead except for the bearing tube. Electrodes such as the ACMI model 12U do not have any means for grasping onto the telescope. It merely has a seat for making sliding contact along the telescope.

It is therefore an objective of the present invention to provide an electrode with a distal end stabilizer that can either slip over the distal end of a telescope or resiliently snap onto the telescope.

SUMMARY OF THE INVENTION

The foregoing problems are overcome and the advantages are provided by an improved electrode for use with a urological endoscope and a method of making the same.

In accordance with one embodiment of the invention, an electrode is provided comprising an electrode lead means; an electrode end means; and an electrode stabilizer means. The electrode stabilizer means can slideably stabilize the electrode proximate a distal region of a telescope. The stabilizer is made of a resilient material for resiliently mounting the electrode to the telescope.

In accordance with another embodiment of the invention, an electrode is provided comprising lead means; electrode end means; stabilizer means; and stiffener means. The stabilizer means has two relatively curved arms and comprises a resilient material for resiliently laterally mounting the stabilizer means onto the telescope. The stiffener means comprises a sleeve covering an insulative cover of the lead means proximate a distal region of the lead means.

In accordance with another embodiment of the invention, an electrode is provided comprising a single elongate conductor and an insulation means. The elongate conductor forms both an elongate lead and has a first end that is bent at a distal region of the electrode to form the electrode end with two substantially parallel arms and an electrode tip therebetween.

In accordance with one method of the invention, a method is provided for manufacturing an electrode comprising the steps of mounting two protective sleeves onto a first conductor; bending the first conductor to form an electrode end; connecting two ends of the first conductor to a second conductor; sliding a protective cover over the second conductor; and connecting a collar to the second conductor proximate the second conductor's proximal region.

BRIEF DESCRIPTION OF THE DRAWINGS

The foregoing aspects and other features of the invention are explained in the following description, taken in connection with the accompanying drawings wherein:

FIG. 1 is a perspective view of a resectoscope electrode assembly incorporating features of the invention.

FIG. 2 is an exploded view of the electrode assembly shown in FIG. 1.

FIG. 3 is a front end view of the stabilizer shown in FIG. 1.

FIG. 4 is a partial perspective view of a single conductor for use in an electrode assembly.

DETAILED DESCRIPTION OF THE INVENTION

Figure 5A:
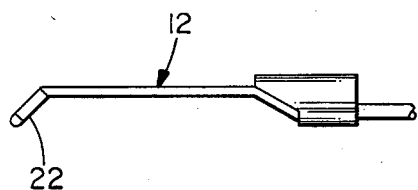
FIG. 5A is a side view of the distal end of an alternate embodiment of the invention.

Referring to FIG. 1, there is shown a perspective view of an electrode assembly 10 comprising features of the present invention. In this embodiment, the electrode assembly 10 is a cutting loop electrode intended for use with a resectoscope. Although the present invention will be described generally with reference to the electrode assembly of FIG. 1, it should be understood that the present invention can be used with various types of electrodes and various different types of medical endoscopes. In addition, it should be understood that the present invention can have any suitable size, shape or type of material for its elements. Cross reference is hereby made to the following copending patent applications: "System For Disconnectably Mounting An Endoscope Sheath With An Endoscope Tool" by Benedetto Grossi, Richard P. Muller and Richard J. O'Hare, Ser. No. 07/202,152, filed June 2, 1988; "Resectoscope With Improved Guide Block And Electrical Plug Connection" by Benedetto Grossi and Raymond Ainger III, Ser. No. 07/202,153, filed June 2, 1988; "System For Reducing Drag On The Movement of An Electrode In A Resectoscope And Method Of Making The Same" by Benedetto Grossi and Thomas W. Bracie, Ser. No. 07/202,154, filed June 2, 1988; Design For A "Resectoscope Electrode", by Benedetto Grossi; Ser. No. 07/262,XXX, filed June 2, 1988; Design For A "Resectoscope Handle and Latch" by Benedetto Grossi; Ser. No. 262,XXX, filed June 2, 1988; and Design For a "Resectoscope Sheath Latch Receptacle" by Benedetto Grossi; Ser. No. 07/262,XXX, filed June 2, 1988 assigned to the same assignee as herein and which are incorporated by reference in their entirety herein.

The electrode assembly 10 generally comprises three main sections; an electrode end 12, an electrode lead 14, and an electrode stabilizer 16. The electrode end 12 generally comprises two substantially parallel arms 18, 20 and an electrode tip 22 at the distal end of the electrode assembly 10 which, in this embodiment, is an electrode cutting loop. Electrode lead 14 is generally comprised of an elongated conductor 24 with an insulative cover 26. The electrode lead 14 generally performs two main functions. First, the lead 14 is connected to an electrosurgical generator (not shown) at its proximal end 28 and can convey electrosurgical current to the electrode end 12 for performing a desired operation. Second, the lead 14 acts as a mechanical connector between a guide block (not shown) in a resectoscope working element and the electrode end 12 such that when an operator moves the guide block (not shown) the operator moves the electrode end 12 correspondingly. The electrode stabilizer 16 generally performs two functions in this embodiment. First, the stabilizer 16 substantially covers and insulates a connection between the lead 14 and the electrode end 12. Second, the stabilizer 16 provides means for attaching the electrode assembly 10 to the distal region of a telescope (not shown) such that the electrode assembly 10 can slideably move relative to the telescope along a predetermined path.

Referring now also to FIG. 2, an exploded view of the individual components that make up the electrode assembly 10 shown in FIG. 1 is shown. The electrode lead 14, in the embodiment shown, generally comprises the elongate conductor 24, the insulative cover 26, a connecting collar 30 and a stiffener 32. The elongate conductor 24 is generally made of metal with a circular cross section and a flattened distal end 34. The insulative cover 26 is generally comprised of a dielectric material and is tube shaped with a central aperture 36 suitably sized to receive the elongate conductor 24 therein. In a preferred embodiment, the length of the cover 26 is slightly less than the length of the elongated conductor 24 such that the elongate conductor 24 will extend past the cover 26 at the proximal end 28 of the electrode assembly 10. The connecting collar 30 can generally be described as a small sleeve that fits over a portion of the proximal end of the elongate conductor 24 and is fixed thereto. The collar 30 is preferably made of a suitable material such as metal and has a center conduit 38 suitably sized and shaped for passage of the elongate conductor 24 therethrough and has an external circular depression 40 on its perimeter. In a preferred embodiment the collar 30 is soldered or welded to the proximal region of the elongate conductor 24 with a portion of the conductor extending past the collar 30 as shown in FIG. 1. The collar 30 generally provides two main functions in this embodiment. First, the collar 30 can substantially prevent the cover 26 from accidentally sliding off the proximal end of the assembly 10 and provides a substantial barrier to the movement of the cover 26 in the proximal direction. Second, the depression 40 and the fact that the collar 30 is fixedly attached to the elongate conductor 24 cooperates with a suitable disconnectable locking mechanism (not shown) in the guide block of a resectoscope working element to fixedly, but removably attach the electrode assembly 10 to the guide block. The stiffener 32 can generally be described as a relatively rigid tube having a central aperture 42 that is suitably sized and shaped to be able to fit over the cover 26 or over the conductor 24 thereby under the cover 26. The stiffener 32 can have any suitable length and is generally provided to give the electrode lead section 14 a certain stiffness for occasions such as when the electrode assembly 10 is advanced along a telescope and a portion of the otherwise relatively flexible electrode lead section 14 extends out past the distal end of an electrode assembly sheath of a resectoscope working element. On occasions such as these, where the relatively flexible electrode lead 14 lacks substantial stiffness, the stiffener 32 can be provided to prevent buckling or bending of the lead 14. In the embodiment shown in FIG. 1, the stiffener 32 is made of metal and has its two ends 44, 46 slightly stamped such that the stiffener 32 is relatively fixedly held on the cover 26. However, any fixation means can be used. In addition, the stiffener 32 may be relatively short and provided merely at the distal region of the lead section 14. Also, the stiffener 32 may be made of any suitably stiff or rigid material such as a reinforced plastic.

Referring now to the electrode end 12, the electrode end 12 generally comprises a second conductor 48, two second sleeves 50, 52 and two outer insulation sleeves 51, 53. The second conductor 48, for the cutting loop assembly, is generally comprised of a tungsten wire which is bent at suitable locations to form a portion of the two arms 18, 20 and the electrode tip 22 connecting the two arms 18, 20 at the distal tip of the assembly 10. The two inner sleeves 50, 52 are placed over the second conductor 48 to add rigidity or stiffness thereto and are bent or deformed with the second conductor; the insulating sleeves 51, 53 being slid onto the inner sleeves 50, 52 after deformation. The two insulating sleeves 51, 53 are generally comprised of a dielectric material such that the second conductor 48 is substantially insulated except at the distal tip. The second conductor 48, in this embodiment, generally has two ends 54, 56 which are substantially exposed such that they can be connected to the distal end 34 of the elongate conductor 24.

The connection between the first elongate conductor 24 and the second conductor 48 generally comprises the distal end 34 of the first conductor 24 and the two ends 54, 56 of the second conductor 48 being inserted into a connector 58 and fixed therein such as by solder. Preferably, the connector 58 has an oval shaped cross section and is made of an electrically conductive material. The oval shape of the connector 58 allows for the two ends 54, 56 of the second conductor and the distal end 34 of a first conductor to be compactly and efficiently orientated in the connector 58. An insulator 60 is generally provided to insulate the connection between the first conductor 24 and the second conductor 48 and substantially surrounds the connector 58. The insulator is generally flexible and can conform to the shape of the connector 58. The insulative cover 26 is generally mounted over one end of the insulator 60. However, in an alternate embodiment, the insulator 60 need not be provided. As will be described below, the stabilizer 16 can provide the insulation for the connection.

The electrode stabilizer 16, in this embodiment, is generally comprised of a resilient and flexible dielectric material. The stabilizer 16 has a connection channel section 62 and a telescope mounting section 64. Referring also to FIG. 3, a front end view of the stabilizer 16 is shown. The connection channel section 62 generally comprises an oval shaped aperture 66 which is suitably sized and shaped to be mounted over the insulator 60 at the connection between the first conductor 24 and the second conductor 48. A suitable means such as a glue or resin is provided to fixedly mount the stabilizer at the connection. The telescope mounting section 64 generally comprises two arms 68, 70 that are intended for making a sliding connection with a telescope. The arms 68, 70 are generally arc shaped and form a telescope seat 72 therebetween. In a preferred embodiment, the stabilizer 16 is made from a molded polymer or plastic material such that the arms 68, 70 which extend upward from the channel section 62 are relatively flexible. The two arms 68, 70 have outer ends 74, 76 which have a first predetermined distance therebetween. In a preferred embodiment the telescope seat 72 substantially mirrors the outer profile of the telescope with the predetermined distance between the outer ends 74, 76 of the stabilizer 16 being less than the diameter or width of the telescope such that the stabilizer can substantially clasp around the outer surface of the telescope.

One of the principal features of the present invention is the ability of the stabilizer 16 to adapt to variations in the distance between the electrode assembly 10 and the telescope. Under ideal circumstances, the electrode assembly 10 moves along an axial path parallel to the telescope. However, due to manufacturing tolerances, assembly tolerances and the like, perfect alignment of the telescope and the intended path of the electrode assembly is never perfectly achieved. Because the electrode assembly 10 has the stiffener 32 which cooperates with the electrode assembly sheath of a working element, the electrode assembly 10 is generally not allowed to bend or flex along its axial path to accommodate for misalignment of the telescope and intended path of the electrode assembly. The resilient nature and adaptability of the stabilizer 16 allows the assembly 10 to move relative to the telescope other than just along an axial path. In the situation where the path of the electrode assembly slightly diverges from the axis of the telescope, the arms 68, 70 of the stabilizer 16 can open or flex out slightly to allow the electrode assembly 10 to substantially continue to move along its intended path while still being retained with the telescope and without any substantial restriction to intended movement.

Because the two arms 68, 70 of the stabilizer 16 are flexible, the stabilizer of the present invention provides another advantage which was heretofore unavailable. Unlike the electrode assemblies presently available which require that their stabilizers be slipped over the distal tip of a telescope for mounting the electrode assembly thereto, the present invention allows for mounting of the electrode assembly not only by slipping the stabilizer 16 over the distal tip of a telescope, but also by laterally snapping the stabilizer onto the telescope. This advantage is particularly advantageous because when an operator is attempting to mount the electrode assembly 10 to a telescope he is simultaneously attempting to mount the proximal end 28 of the electrode lead 14 into a relatively small aperture in a guide block of the resectoscope working element. Because the operator is attempting to make two separate connections at two opposite locations on the electrode assembly at the same time an operator can often miss one of the connections and thus have to withdraw the previously completed connection in order to successfully complete both connections. The present invention allows not only for the operator to make both connections at the same time, but also allows for the operator to first make a first connection between the proximal end of the lead 14 and the guide block of the resectoscope working element and then laterally snapping the stabilizer 16 onto the telescope making the second connection.

The snap-on connection of the stabilizer 16 to a telescope will now be described. As stated above, the arms 68, 70 of the stabilizer 16 are resilient and flexible. An operator, by placing the outer ends 74, 76 of the arms next to the side of a telescope, can push the channel section 62 towards the telescope. With this force, the telescope will force the arms 68, 70 to bow outwardly moving the ends 74, 76 from their first predetermined distance whereby the telescope seat 72 will start to advance on to the telescope. The arms 68, 70 are generally provided with enough resiliency such that the ends 74, 76 can move to a second position with a predetermined distance therebetween substantially equivalent to the width or diameter of the telescope being mounted therewith. Once the widest portion of the telescope passes the ends 74, 76 into the seat area 72, the force caused by the deflection of the arms 68, 70 and the shape of the telescope can effectively cooperate to quickly mount the telescope in the telescope seat 72. With the telescope located in the telescope seat 72, the electrode assembly 10 is slidably connected to the telescope for axial movement relative thereto. In a preferred embodiment the shape of the seat 72 and arms 68, 70 along with a predetermined degree of flexibility or resiliency therein combine to substantially prevent the stabilizer 16 from being dislodged or disconnected from the telescope other than by axially moving the electrode assembly 10 off of the telescope via the telescope distal tip. However, the stabilizer 16 may be formed such that it can be laterally removed from the telescope with the operator applying a small amount of force.

Referring now also to FIG. 4, an alternate embodiment of the invention will be described. In this embodiment of the invention, a single conductor 78 is provided for both the single electrode lead section 14 and the electrode end section 12. The single conductor 78 has a first end (not shown) that forms the proximal end of the electrode assembly and a second end 80 that is suitably deformed or bent to form the electrode end having two substantially parallel arms 18, 20 and an electrode tip 22. A distal tip 82 is suitably deformed back towards the electrode lead section 14 and can be connected thereto via a connector (not shown) and suitable fixation means such as solder. Of course, suitable insulation sleeves are provided on the arms 18, 20 and an insulation cover would be provided for the electrode lead section 14 such that the single electrode assembly of FIG. 4 would look substantially similar to the electrode assembly shown in FIG. 1. However, manufacturing costs for manufacturing a single conductor electrode assembly may be substantially reduced.

Figure 5B:
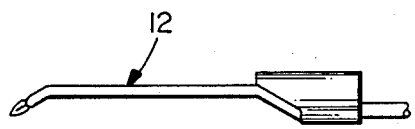
FIG. 5B is a side view of the distal end of an alternate embodiment of the invention.
Figure 5C:
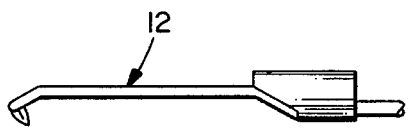
FIG. 5C is a side view of the distal end of an alternate embodiment of the invention.
Figure 5D:
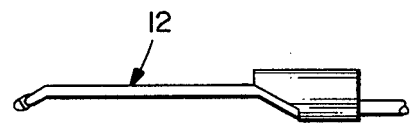
FIG. 5D is a side view of the distal end of an alternate embodiment of the invention.
Figure 5E:
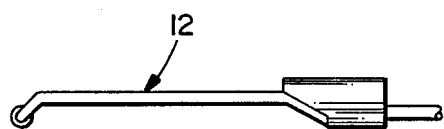
FIG. 5E is a side view of the distal end of an alternate embodiment of the invention.

Referring now to FIGS. 5A, B, C, D and E, various different electrode assemblies are shown. FIG. 5A shows the electrode end of an electrode assembly wherein the distal tip 22 is provided as a coagulating electrode. FIG. 5B shows the electrode end 12 of an electrode assembly wherein the distal tip 22 comprises a knife electrode. FIG. 5C shows the electrode end 12 of an electrode assembly having an electrode tip 22 comprising a retrograde knife electrode. FIG. 5D shows an electrode end 12 of an electrode assembly having an electrode tip comprising a punctate electrode. FIG. 5E shows an electrode end 12 of an electrode assembly having an electrode tip 22 comprising a roller electrode. For an electrode assembly comprising a single conductor as described with reference to FIG. 4 having a roller thereon, it may be desirous to place the roller on the conductor 78 prior to deforming the conductor 78 or prior to completion of deformation.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. An electrode assembly for use with an endoscope, the assembly comprising:
   electrode lead means having an elongate conductor with an insulative cover;
   electrode end means having a pair of parallel arms connected at a distal tip of the electrode assembly by an electrode tip and having stiffener means operatively attached to said pair of parallel arms for stiffening said electrode lead means; and
   electrode stabilizer means for slideably stabilizing the electrode proximate a distal region of a telescope, said stabilizer means being made of a resilient and flexible dielectric material for resiliently laterally mounting the electrode to the telescope and for insulating the electrode assembly from the telescope.

2. An assembly as in claim 1 wherein said stabilizer means is comprised of a polymer material.

3. As assembly as in claim 1 wherein said stabilizer means comprises at least two arms with a predetermined distance between outer ends of said arms.

4. An assembly as in claim 3 wherein said two arms form a telescope seat for matingly receiving the telescope, said predetermined distance being less than the width of the telescope.

5. An assembly as in claim 4 wherein said arms can flex to increase said predetermined distance to allow the electrode to laterally snap onto the telescope or to accommodate spatial variations relative to the telescope without inducing significant resistance to movement of the electrode assembly.

6. An assembly as in claim 4 wherein said arms can slip over the distal tip of the telescope to slidingly attach the electrode to the telescope.

7. An assembly as in claim 1 wherein said stabilizer means has a connection channel for mounting at least a portion of said lead means and end means therein.

8. An assembly as in claim 5 wherein said arms can slip over the distal tip of the telescope to remove the electrode from the telescope.

9. An electrode assembly for use with a urological endoscope, the electrode comprising:
   lead means having a first elongate conductor and an insulative cover;
   electrode end means having a pair of parallel arms connected at a distal tip of the electrode by an electrode tip, said electrode end means comprising a second conductor, said parallel arms comprising said second conductor and outer protective sleeves;
   stabilizer means for stabilizingly connecting the electrode with a telescope for relative movement thereto, said stabilizer means having two relatively curved arms and comprising a resilient and flexible dielectric material such that the assembly can be resiliently laterally mounted onto the telescope and the electrode assembly can be insulated from the telescope; and
   stiffener means for stiffening the distal region of said lead means, said stiffener means comprising a sleeve covering said insulative cover proximate a distal region of said lead means.

10. An assembly as in claim 9 wherein said second conductor is comprised of tungsten.

11. An assembly as in claim 9 wherein said first and second conductors are connected to each other with a connector therearound.

12. An assembly as in claim 11 wherein said first conductor has a relatively flat distal end.

13. An electrode assembly for use with a urological endoscope, the electrode comprising:
   lead means having a first elongate conductor and an insulative cover;
   electrode end means having a pair of parallel arms connected at a distal tip of the electrode by an electrode tip, said electrode end means comprising a second conductor, said parallel arms comprising said second conductor and outer protective sleeves;
   stabilizer means for stabilizingly connecting the electrode with a telescope for relative movement thereto, said stabilizer means having two relatively curved arms and comprising a resilient material such that the assembly can be resiliently laterally mounted onto the telescope and having an oval shaped chamber covering a connection between said first and second conductors; and
   stiffener means for stiffening the distal region of said lead means, said stiffener means comprising a sleeve covering said insulative cover proximate a distal region of said lead means.

14. An assembly as in claim 13 further comprising a relatively short insulator between said connection and said stabilizer means.

15. An assembly as in claim 13 wherein said stiffener means comprises a rigid tube.

16. An assembly as in claim 13 further comprising a proximal end conductor sleeve fixed to a proximal region of said first conductor and having a depression for removably attaching the proximal end of said first conductor to the endoscope.

* * * * *